(12) United States Patent
Crawforth et al.

(10) Patent No.: US 7,161,006 B2
(45) Date of Patent: Jan. 9, 2007

(54) SULPHONES FOR INHIBITION OF GAMMA SECRETASE

(75) Inventors: James Michael Crawforth, Watton-at-Stone (GB); Jason Matthew Elliott, Felsted (GB); Andrew Pate Owens, Huntingdon (GB); Francine Sternfeld, London (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 138 days.

(21) Appl. No.: 10/528,214

(22) PCT Filed: Sep. 25, 2003

(86) PCT No.: PCT/GB03/04173

§ 371 (c)(1),
(2), (4) Date: Mar. 17, 2005

(87) PCT Pub. No.: WO2004/037138

PCT Pub. Date: Apr. 15, 2004

(65) Prior Publication Data

US 2005/0261276 A1    Nov. 24, 2005

(30) Foreign Application Priority Data

Oct. 4, 2002    (GB) ................ 0223040.7

(51) Int. Cl.
*C07D 215/16*    (2006.01)
*C07D 333/32*    (2006.01)
*C07D 277/04*    (2006.01)
*C07D 261/04*    (2006.01)
*C07C 303/00*    (2006.01)
*A01N 43/42*    (2006.01)
*A01N 43/56*    (2006.01)

(52) U.S. Cl. ............ 546/153; 549/65; 548/185; 548/243; 548/366.7; 564/85; 564/86; 564/87; 564/88; 564/89; 564/90; 564/92; 514/312; 514/369; 514/380; 514/407

(58) Field of Classification Search ............ 549/65; 546/153; 548/185, 243, 366.7; 564/85–90, 564/92; 514/312, 369, 380, 407, 445

See application file for complete search history.

(56) References Cited

FOREIGN PATENT DOCUMENTS

WO    WO 00/50391    8/2000

*Primary Examiner*—J. Parsa
(74) *Attorney, Agent, or Firm*—John C. Todaro; Melvin Winokur

(57) ABSTRACT

The invention provides compounds of formula I:

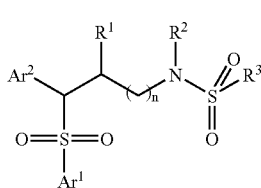

which are inhibitors of γ-secretase and hence useful in the treatment or prevention of Alzheimer's disease.

8 Claims, No Drawings

SULPHONES FOR INHIBITION OF GAMMA SECRETASE

CROSS REFERENCE TO RELATED APPLICATIONS

This application is a U.S. National Phase application under 35 U.S.C. § 371 of PCT Application No. PCT/GB2003/004173, filed Sep. 25, 2003, which claims priority under 35 U.S.C. § 119 from GB Application No. 0223040.7, filed Oct. 4, 2002.

The present invention relates to a novel class of compounds, their salts, pharmaceutical compositions comprising them, processes for making them and their use in therapy of the human body. In particular, the invention relates to novel sulphones which inhibit the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards γ-secretase, as measured in cell-based assays. These are reviewed in WO 01/70677. Many of the relevant compounds are peptides or peptide derivatives.

WO 00/50391 discloses a broad class of sulphonamides as modulators of the production of β-amyloid, but neither discloses nor suggests the compounds of the present invention.

The present invention provides a novel class of sulphones which are useful in the treatment or prevention of AD by inhibiting the processing of APP by the putative γ-secretase, thus arresting the production of Aβ.

According to the present invention there is provided a compound of formula I:

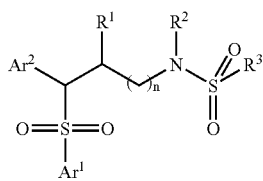

where n is 2, 3 or 4;

$Ar^1$ represents phenyl or heteroaryl, either of which bears 0–3 substituents independently selected from halogen, CN, $NO_2$, $CF_3$, $GHF_2$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$Ar^2$ represents phenyl or heteroaryl, either of which bears 0–3 substituents independently selected from halogen, CN, $NO_2$, $CF_3$, $CHF_2$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$R^1$ represents $C_{1-4}$alkyl, or together with $R^2$ completes a pyrrolidine, piperidine or homopiperidine ring;

$R^2$ represents H or $C_{1-6}$alkyl which optionally bears a substituent selected from halogen, CN, $NO_2$, $CF_3$, OH and $C_{1-4}$alkoxy; or together with $R^1$ completes a pyrrolidine, piperidine or homopiperidine ring; or together with $R^3$ completes a tetrahydroisothiazole-1,1-dioxide ring; and $R^3$ represents phenyl, naphthyl or heteroaryl, any of which may bear up to 3 substituents selected from halogen, CN, $NO_2$, $CF_3$, $CHF_2$, OH, $OCF_3$, $C_{1-4}$alkoxy, $C_{1-4}$alkoxycarbonyl, $C_{2-6}$acyl, $C_{2-6}$acyloxy, $C_{2-6}$acylamino, amino, $C_{1-4}$alkylamino, di($C_{1-4}$alkyl)amino or $C_{1-4}$alkyl which optionally bears a substituent selected from halogen, CN, $NO_2$, $CF_3$, OH and $C_{1-4}$alkoxy; or $R_3$ represents $CF_3$ or a non-aromatic hydrocarbon group of up to 6 carbon atoms optionally bearing one substituent selected from halogen, CN, $CF_3$, OH, $OCF_3$, $C_{1-4}$alkoxy, $C_{1-4}$alkoxycarbonyl, $C_{2-6}$acyl, $C_{2-6}$acyloxy, $C_{2-6}$acylamino, amino, $C_{1-4}$alkylamino, di($C_{1-4}$alkyl)amino or phenyl, naphthyl or heteroaryl, any of which may bear up to 3 substituents selected from halogen, CN, $NO_2$, $CF_3$, $CHF_2$, OH, $OCF_3$, $C_{1-4}$alkoxy, $C_{1-4}$alkoxycarbonyl, $C_{2-6}$acyl, $C_{2-6}$acyloxy, $C_{2-6}$acylamino, amino, $C_{1-4}$alkylamino, di(C 1-4alkyl)amino or $C_{1-4}$alkyl which optionally bears a substituent selected from halogen, CN, $NO_2$, $CF_3$, OH and $C_{1-4}$alkoxy; or $R^3$ together with $R^2$ completes a tetrahydroisothiazole-1,1-dioxide ring;

or a pharmaceutically acceptable salt thereof.

In a particular embodiment of the invention, when n is 2 and $R^1$ and $R^3$ are both $CH_3$ and $R^2$ is H and $Ar^1$ is 4-chlorophenyl and $Ar^2$ is 2,5-difluorophenyl, the compound of formula I is in the more polar of the two possible diastereomeric forms. A measure of the relative polarity of the said diastereoisomers is their respective retention times on a HPLC column, the more polar diastereoisomer having the longer retnetion time.

As used herein, the expression "non-aromatic hydrocarbon group" refers to any group consisting of carbon and hydrogen atoms only, but not comprising an aromatic ring, up to an indicated maximum number of carbon atoms. The term therefore encompasses alkyl, alkenyl, alkynyl, cycloalkyl and cycloalkenyl moieties, singly or in any combination.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl isopropyl and t-butyl. Derived expressions such as "$C_{2-6}$alkenyl", "hydroxy-$C_{1-6}$alkyl", "heteroaryl$C_{1-6}$alkyl", "$C_{2-6}$alkynyl" and "$C_{1-6}$alkoxy" are to be construed in an analogous manner.

The expression "$C_{2-6}$acyl" as used herein refers to $C_{1-5}$alkylcarbonyl groups in which the alkyl portion may be straight chain, branched or cyclic, and may be halogenated. Examples include acetyl, propionyl and trifluoroacetyl.

The expression "heteroaryl" as used herein means a monocyclic system of 5 or 6 ring atoms, or fused bicyclic system of up to 10 ring atoms, selected from C, N, O and S, wherein at least one of the constituent rings is aromatic and comprises at least one ring atom which is other than carbon. Examples of heteroaryl groups include pyridinyl pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, benzenesulphonic acid, methanesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. Unless expressly indicated otherwise, it is to be understood that all such isomers and mixtures thereof in any proportion are encompassed within the scope of the present invention.

In the compounds of formula I, n is preferably 2 or 3, most preferably 2.

In the compounds of formula I, $Ar^1$ represents optionally substituted phenyl or heteroaryl. Typical heteroaryl embodiments of $Ar^1$ are 6-membered, such as optionally substituted pyridyl, in particular optionally substituted 3-pyridyl. $Ar^1$ is preferably selected from 6-(trifluoromethyl)-3-pyridyl and phenyl groups substituted in the 4-position with halogen, methyl or mono-, di- or trifluoromethyl. In a preferred embodiment of the invention $Ar^1$ represents 4-chlorophenyl. In another preferred embodiment $Ar^1$ represents 4-trifluoromethylphenyl.

$Ar^2$ preferably represents optionally substituted phenyl, in particular phenyl bearing 2 or 3 halogen substituents. $Ar^2$ is typically selected from phenyl groups bearing halogen substituents (preferably fluorine) in the 2- and 5-positions or in the 2-, 3- and 6-positions. In a preferred embodiment of the invention, $Ar^2$ represents 2,5-difluorophenyl.

In a particular embodiment, $Ar^1$ is 4-chlorophenyl or 4-trifluoromethylphenyl and $Ar^2$ is 2,5-difluorophenyl.

In one embodiment of the invention, $R^1$ represents $C_{1-4}$alkyl, such as methyl, ethyl propyl or butyl. Within this embodiment, $R^1$ is preferably methyl.

In an alternative embodiment, $R^1$ and $R^2$ complete a pyrrolidine, piperidine or homopiperidine ring, preferably a pyrrolidine or piperidine ring, and most preferably a piperidine ring. Thus, $R^1$ and $R^2$ together may represent $(CH_2)_m$ where m is 1, 2 or 3 such that (n+m) is 3, 4 or 5. Within this embodiment, n is preferably 2 and m is preferably 1 or 2. Most preferably, n and m are both 2.

When $R^1$ represents $C_{1-4}$alkyl, $R^2$ represents H or optionally-substituted $C_{1-6}$alkyl, or together with $R^3$ completes a tetrahydroisothiazole-1,1-dioxide ring. In this embodiment, $R^2$ is typically selected from H and methyl, ethyl, propyl or butyl which are optionally substituted with halogen, OH, CN, methoxy or $CF_3$, or $R^2$ together with $R^3$ represents $(CH_2)_3$. In this embodiment, preferably $R^2$ represents H, methyl or 2,2,2-trifluoroethyl, or together with $R^3$ represents $(CH_2)_3$.

When $R^2$ represents H or optionally-substituted $C_{1-6}$alkyl, or forms a ring with $R^1$, $R^3$ is selected from optionally-substituted phenyl, naphthyl or heteroaryl, $CF_3$, and optionally-substituted hydrocarbon of up to 6 carbon atoms. In one embodiment, $R^3$ represents optionally-substituted phenyl, naphthyl or heteroaryl, preferably optionally-substituted phenyl or heteroaryl. When aryl or heteroaryl groups represented by $R^3$ bear more than one substituent, said substituents are preferably halogen atoms (especially chlorine or fluorine) or alkyl groups (especially methyl). Within this embodiment, $R^3$ aptly represents optionally-substituted phenyl, thiophene, quinoline, thiazole, isoxazole or pyrazole. Preferred substituents include halogen (especially chlorine, bromine or fluorine), alkyl (especially methyl), alkoxycarbonyl (such as methoxycarbonyl) and acylamino (such as acetylamino). Preferred examples of aryl or heteroaryl groups represented by $R^3$ include phenyl, 2-thienyl, 3-chloro-2-thienyl, 5-chloro-2-thienyl, 3-bromo-2-thienyl, 8-quinolinyl, 2-methoxycarbonyl-3-thienyl, 2-acetylamino-4-methylthiazol-5-yl, 3,5-dimethylisoxazol-4-yl and 1,3,5-trimethylpyrazol-4-yl.

In an alternative embodiment $R^3$ represents $CF_3$ or a non-aromatic hydrocarbon group of up to 6 carbon atoms which is optionally substituted as described previously. When a phenyl, naphthyl or heteroaryl substituent is present, said substituent may itself bear up to 3 substituents as described earlier. Preferably, said phenyl, naphthyl or heteroaryl substituent itself bears at most one substituent that is other than halogen or alkyl, and most preferably is unsubstituted. Suitable hydrocarbon groups include alkyl, such as methyl, ethyl, n-propyl, isopropyl or t-butyl, and alkenyl, such as vinyl or allyl. Preferred substituents include halogen (especially chlorine) and phenyl. Preferred examples of optionally-substituted hydrocarbon groups represented by $R^3$ include methyl, isopropyl, 3-chloropropyl, benzyl and styryl.

In particularly preferred embodiments of the invention, $R^3$ is selected from methyl, isopropyl, 2-thienyl, benzyl and, in combination with $R^2$, $(CH_2)_3$.

A sub-class of the compounds of the invention are defined by formula II:

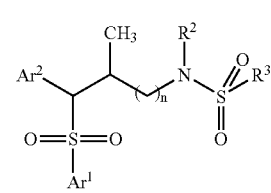

II where n, $Ar^1$, $Ar^2$, $R^2$ and $R^3$ have the same definitions and preferred identities as before;

and pharmaceutically acceptable salts thereof.

Preferably, n is 2 or 3, and most preferably n is 2.

In a first subset of the compounds of formula II, $R^2$ represents H, methyl or 2,2,2-trifluoroethyl.

In a second subset of the compounds of formula II, $R^2$ and $R^3$ together represent $(CH_2)_3$.

It will be readily apparent that in the compounds of formula II the carbon atom to which $Ar^2$ is attached and the carbon atom to which the methyl group is attached are chiral centres, giving rise to two diastereomeric and four enantiomeric forms. All these possible isomeric forms, singly or in mixtures of any proportion, are within the scope of the invention. However, when n is 2 and $R^2$ is H and $R^3$ is $CH_3$ and $Ar^1$ is 4-chlorophenyl and $Ar^2$ is 2,5-difluorophenyl, the more polar of the two diastereomeric forms is preferred. This preferred diastereoisomer exists in two entantiomeric forms, and that which elutes second under the conditions described in example 1 is preferred.

A second subclass of the compounds of the invention are defined by formula III:

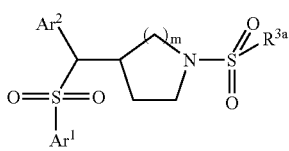

where m, $Ar^1$ and $Ar^2$ have the same definitions and preferred identities as before, and $R^{3a}$ represents $R^3$ which does not form a ring with $R^2$; and pharmaceutically acceptable salts thereof.

Preferably m is 2.

In a preferred subset of the compounds of formula III, $R^{3a}$ is methyl, $CF_3$, 2-thienyl or 3-chloro-2-thienyl.

Examples of individual compounds in accordance with formula I are provided in the Examples section appended hereto.

The compounds of formula I have an activity as modulators of the processing of APP by γ secretase.

The invention also provides pharmaceutical compositions comprising one or more compounds of formula I or the pharmaceutically acceptable salts thereof and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 250 mg, for example 1, 2, 5, 10, 25, 50, 100, 200 or 250 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil or coconut oil as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

The present invention further provides a method of treatment of a subject suffering from or prone to a condition associated with the deposition of β-amyloid which comprises administering to that subject an effective amount of a compound according to formula I or a pharmaceutically acceptable salt thereof. Preferably the condition is a neurological disease having associated β-amyloid deposition such as Alzheimer's disease.

For treating or preventing Alzheimer's Disease, a suitable dosage level is about 0.01 to 250 mg/Kg per day, preferably about 0.10 to 100 mg/Kg per day, especially about 1.0 to 50 mg/Kg, and for example about 10 to 30 mg/Kg of body weight per day. Thus, a dose of about 500 mg per person per day may be considered. The compounds may be administered on a regimen of 1 to 4 times per day. In some cases, however, dosage outside these limits may be used.

Compounds of formula I in which $R^2$ does not form a ring with $R^3$ may be prepared by reaction of an amine (IV) with $R^{3a}$—$SO_2Cl$:

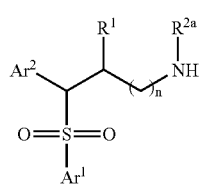

where $R^{2a}$ represents $R^2$ which does not complete a ring with $R^3$, and n, $Ar^1$, $Ar^2$, $R^1$ and $R^{3a}$ have the same meanings as before. The reaction may be carried out at ambient temperature in an aprotic solvent such as dichloromethane in the presence of a base such as pyridine.

Compounds of formula I in which $R^2$ and $R^3$ together complete a tetrahydroisothiazole-1,1-dioxide ring may be prepared by reaction of an amine IV in which $R^{2a}$ is H with L—$(CH_2)_3$—$SO_2Cl$, where L represents a leaving group such as halogen, followed by intramolecular alkylation of the resulting sulphonamide nitrogen. Said alkylation may be carried out in refluxing toluene in the presence of sodium hydride.

Amines of formula IV in which $R^{2a}$ is H may be prepared by reduction of nitriles V:

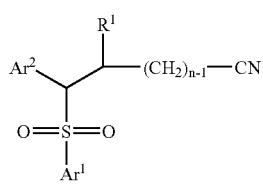

V where n, $Ar^1$, $Ar^2$ and $R^1$ have the same meanings as before. The reduction may be carried out using borane in THF at 50° C.

The nitriles of formula V may be prepared by alkylation of sulphones VI with electrophiles VII:

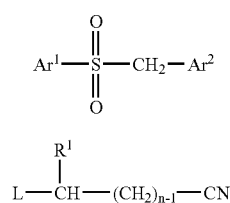

VI

VII where L, n, $Ar^1$, $Ar^2$ and $R^1$ have the same meanings as before.

The nitriles V in which n is 2 are more easily prepared by addition of sulphones VI to cyanoalkenes VIII:

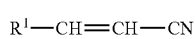

VIII where $R^1$ has the same meaning as before. The reaction may be carried out in THF at 0° C. in the presence of sodium hydride.

The sulphones VI are prepared as described in U.S. 2003/0114496 A1.

Amines of formula IV in which $R^{2a}$ is alkyl may be prepared by N-alkylation of the corresponding primary amines IV in which $R^{2a}$ is H. Alternatively, the nitriles V may be converted to the corresponding aldehydes by treatment with diisobutylaluminium hydride followed by hydrolysis, and the aldehydes reacted with $R^{2a}NH_2$ and sodium triacetoxyborohydride. The reaction with DIBAL is typically carried out at −40° C. in dichloromethane, and the second step at ambient temperature in dichloromethane in the presence of acetic acid.

Amines of formula IV in which $R^1$ and $R^{2a}$ complete a ring are available by reaction of a mesylate of formula XII with the carbanion derived from a sulphone VI:

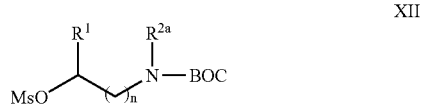

XII where BOC represents t-butoxycarbonyl, Ms represents methanesulphonyl and $R^1$ and $R^{2a}$ complete a ring, followed by removal of the BOC protecting group. The carbanion is formed by treating VI with sodium hydride in THF at 0° C., and is typically reacted with the mesylate in situ in refluxing THF.

Where they are not commercially available, the starting materials $R^{3a}$—$SO_2Cl$, VII, VIII, X, XI and XII may be prepared by methods known to those skilled in the art. It will also be apparent to those skilled in the art that certain compounds in accordance with formula I, prepared by the above-described methods, may be converted into other compounds within the definition of formula I using standard techniques of organic synthesis. For example, compounds of formula I in which $R^2$ is H may be subjected to N-alkylation to provide corresponding compounds in which $R^2$ is alkyl or substituted alkyl.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers and diastereoisomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, 3rd ed., John Wiley & Sons, 1999. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT, are cultured at 50–70% confluency. 10 mM sodium butyrate is added 4 hours prior to plating.

2) Cells are plated in 96-well plates at 35,000 cells/well/100 μL in Dulbeccos minimal essential medium (DMEM) (phenol red-free)+10% foetal bovine serum (FBS), 50 mM HEPES buffer (pH7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% $CO_2$.
5) Prepare reagents necessary to determine amyloid peptide levels, for example by Homogeneous Time Resolved Fluorescence (HTRF) assay.
6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4–0.8. (Mix briefly before reading to disperse the reduced formazan product).
11) Quantitate amyloid beta 40 peptide using an HTRF plate reader.

Alternative assays are described in *Biochemistry*, 2000, 39(30), 8698–8704.

See also, *J. Neuroscience Methods*, 2000, 102, 61–68.

The Examples of the present invention all had an $ED_{50}$ of less than 1 μM, typically less than 0.5 μM, in most cases less than 100 nM, and in preferred cases less than 10 nM, in at least one of the above assays.

The following examples illustrate the present invention.

EXAMPLES

Intermediate A

2-[(4-Chlorobenzenesulfonyl)methyl]-1,4-difluorobenzene prepared as described in U.S. 2003/0114496 A1 (page 8, Intermediate 1).

Example 1

(3RS, 4RS)-N-[4-(4-Chlorobenzenesulfonyl)-4-(2,5-difluorophenyl)-3-methylbutyl]-methanesulfonamide a) To a solution of Intermediate A (20.1 g; 66.6 mmol) in dry THF (200 ml) at 0° C. was added sodium hydride (60% dispersion in oil; 3.2 g; 79.9 mmol) and the mixture was stirred for 30 minutes. Crotononitrile (8.1 ml; 99.9 mmol) was added slowly and stirring continued for 18 hours at room temperature. The reaction was quenched with water (200 ml), extracted with ethyl acetate (4×100 ml) and the combined organics were dried ($MgSO_4$) and concentrated in vacua. The crude residue was purified by flash chromatography eluting 5 to 25% ethyl acetate in isohexanes to yield, as a mixture of diastereoisomers, (3RS,4RS)-4-(4-chlorobenzenesulfonyl)-4-(2,5-difluorophenyl)-3-methylbutyronitrile as a cream solid, (14.1 g, 57%).

$\delta_H$ (360 MHz, $CDCl_3$) 1.1 and 1.6 (total 3H, d, J=6.7 Hz), 2.21 and 2.63 (total 1H, 2×dd, J=7.6, 16.8, and J=3.8, 16.8 Hz), 2.90 and 3.14 (total 1H, 2×dd, J=3.7, 16.5 and J=6.4, 16.5 Hz), 3.04–3.09 (1H, m), 4.54–4.58 (1H, m), 6.75–6.85 (1H, m), 6.93–7.01 (1H, m), 7.31–7.36 (3H, m), 7.47–7.54 (2H, m).

b) To a solution of (3RS, 4RS)-4-(4-chlorobenzenesulfonyl)-4-(2,5-difluorophenyl)-3-methylbutyronitrile (2 g, 5.42 mmol) in THF (30 ml) was added borane (1M solution in THF, 6.5 ml, 6.5 mmol) and the mixture was heated at 50° C. for 20 hours. The mixture was cooled to room temperature and quenched with methanol (50 ml) and HCl (2M, 5 ml), then heated at reflux for one hour. The cooled reaction mixture was concentrated in vacuo and purified by flash chromatography eluting with 2% to 10% methanol in dichloromethane, to give as a mixture of diastereoisomers (3RS, 4RS)-4-(4-chlorobenzenesulfonyl)-4-(2,5-difluorophenyl)-3-methylbutylamine as a white solid (1.7 g, 84%).

$\delta_H$ (360 MHz, $CDCl_3$) 1.10 and 1.38 (total 3H, d, J=7.9 Hz), 1.41–1.52 (1H, m), 1.63–1.70 and 1.80–1.90 (total 1H, m), 2.60–2.94 (3H, m), 4.46 (1H, m), 6.70–6.81 (1H, m), 6.89–6.97 (1H, m), 7.29–7.34 (2H, m), 7.42–7.53 (3H, m), m/z ($ES^+$) 374 ($MH^+$).

c) To (3RS, 4RS-4-(4-chlorobenzenesulfonyl)-4-(2,5-difluorophenyl)-3-methylbutylamine, (0.1 g, 0.268 mmol), and pyridine (0.045 ml; 0.54 mmol) in dichloromethane (5 ml) was added methanesulfonyl chloride (0.03 ml, 0.40 mmol) and the mixture was stirred for 24 hours at room temperature. The mixture was diluted with water (5 ml), the phases were separated, and the organic layer was washed with brine, (5 ml), dried ($MgSO_4$) and evaporated under reduced pressure. The crude product was purified by preparative HPLC to yield the title compound as a white solid (50 mg, 42%).

Diastereoisomers were separated by preparative HPLC (Supelcosil™ ABZ+plus column (100×212 mm) with a mobile phase of 50% acetonitrile:50% (0.1% TFA) water) and then into the single enantiomers of the more polar diastereoisomer pair by chiral preparative HPLC (chiral OJ column (250×21 mm) with a mobile phase of 70% ethanol: 30% iso-hexane, flow rate 4.5 ml/min).

First to elute (Diastereoisomer 1)-$\delta_H$ (400 MHz, DMSO-d) 0.85–0.89 (1H, m), 1.25 (3H, d, J=6.6 Hz), 1.53–1.56 (1H, m), 2.71–2.74 (1H, m), 2.81 (3H s), 2.89–2.96 (2H, m), 4.70 (1H, d, J=8.8 Hz), 6.91 (1H, t, J=8.8 Hz), 7.04–7.09 (1H, m), 7.18–7.21 (1H, m), 7.36 (1H, broad s), 7.54–7.62 (4H, m); m/z ($ES^+$) 452 ($MH^+$).

Second to elute (Diastereoisomer 2)-$\delta_H$ (400 MHz, DMSO-$d_6$), 0.85–0.87 (1H, m), 0.99 (3H, d, J=6.7 Hz), 1.28–1.40 (1H, m), 2.81–2.82 (1H, m), 2.89 (3H, s), 2.97–3.06 (2H, m), 4.76 (1H, d, J=6.6 Hz), 7.02 (1H, m), 7.10–7.14 (1H, m), 7.21–7.25 (1H, m), 7.38–7.42 (1H, m), 7.57–7.62 (2H, m), 7.62–7.6 (2H, m); m/z ($ES^+$) 452 ($MH^+$).

First to elute (Enantiomer 1)-$\delta_H$ (400 MHz, $CDCl_3$) 0.87–0.92 (1H, m), 1.26 (3H, d, J=7.6 Hz), 1.26–1.44 (1H, m), 2.83–2.86 (1H, m), 2.94 (3H, s), 3.11–3.17 (1H, m), 3.23–3.27 (1H, m), 4.48 (1H, d, J=7.8 Hz), 6.77–6.83 (1H, m), 6.93–6.98 (1H, m), 7.32–7.35 (2H, m), 7.44 (1H, broad s), 7.49–7.53 (2H, m); m/z ($ES^+$) 452 ($MH^+$).

Second to elute (Enantiomer 2)-$\delta_H$ (400 MHz, $CDCl_3$) 0.87–0.91 (1H, m), 1.27 (3H, d, J=7.6 Hz), 1.29–1.44 (1H, m), 2.79–2.87 (1H, m), 2.94 (3H, s), 3.11–3.16 (1H, m), 3.23–3.26 (1H, m), 4.48 (1H, d, J=6.9 Hz), 6.77–6.83 (1H, m), 6.94–6.97 (1H, m), 7.33–7.35 (2H, m), 7.44 (1H, broad s), 7.69–7.71 (2H, m), m/z ($ES^+$) 452 ($MH^+$).

Examples 2–13 were prepared by the procedure of Example 1, using the appropriate sulfonyl chloride in Step (c):

Example 2

(3RS, 4RS)-N-[4-(4-chlorobenzenesulfonyl)-4-(2,5-difluorophenyl)-3-methylbutyl]-thiophene-2-sulfonamide m/z (ES$^+$) 520 (MH$^+$).

Example 3

(3RS 4RS)-N-[4-(4-chloro-benzenesulfonyl)-4-(2,5-difluoro-phenyl)-3-methyl-butyl]-isopropylsulfonamide m/z (ES$^+$) 478 (MH$^+$).

Example 4

(3RS, 4RS)-N-[4-(4-Chloro-benzenesulfonyl)-4-(2,5-difluoro-phenyl)-3-methyl-butyl]-phenylmethanesulfonamide m/z (ES$^+$) 528 (MH$^+$).

Example 5

(3RS, 4RS)-N-[4-(4-chloro-benzenesulfonyl)-4-(2,5-difluoro-phenyl)-3-methyl-butyl]-quinoline-8-sulfonamide m/z (ES$^+$) 564 (MH$^+$).

Example 6

(3RS, 4R)-N-[4-(4-Chloro-benzenesulfonyl)-4-(2,5-difluoro-phenyl)-3-methyl-butyl]-phenylsulfonamide m/z (ES$^+$) 515 (MH$^+$).

Example 7

(3RS, 4RS)-Methyl-[4-(4-chloro-benzenesulfonyl)-4-(2,5-difluoro-phenyl)-3-methyl-butylsulfamoyl]-thiophene-2-carboxylate m/z (ES$^+$) 578 (M$^+$).

Example 8

(3RS 4RS)-N-{2-[4-(4-Chlorobenzenesulfonyl)-4-(2,5-difluorophenyl)-3-methylbutylsulfamoyl]-4-methylthiazol-5-yl}acetamide m/z (ES$^+$) 593 (MH$^+$).

Example 9

(3RS, 4RS)-N-[4-(4-chlorobenzenesulfonyl)-4-(2,5-difluorophenyl)-3-methylbutyl]-5-chlorothiophene-2-sulfonamide m/z (ES$^+$) 554 (MH$^+$).

Example 10

(3RS, 4RS)-N-[4-(4-chlorobenzenesulfonyl)-4-(2,5-difluorophenyl)-3-methylbutyl]-3,5-dimethylisoxazole-4-sulfonamide m/z (ES$^+$) 533 (MH$^+$).

Example 11

(3RS, 4RS)-N-[4-(4-chloro-benzenesulfonyl)-4-(2,5-difluoro-phenyl)-3-methyl-butyl]-2-phenylethenesulfonamide m/z (ES$^+$) 540 (MH$^+$).

Example 12

(3RS 4RS)-N-[4-(4-chloro-benzenesulfonyl)-4-(2,5-difluoro-phenyl)-3-methyl-butyl]-5-chloro-1,3-dimethyl-1H-pyrazole-4-sulfonamide m/z (ES$^+$) 566 (MH$^+$).

Example 13

(3RS, 4RS)-N-[4-(4-chloro-benzenesulfonyl)-4-(2,5-difluoro-phenyl)-3-methyl-butyl]-4-chlorobenzenesulfonamide m/z (ES$^+$) 548 (MH$^+$).

Example 14

(3RS 4RS)-2-[4-(4-Chlorobenzenesulfonyl)-4-(2,5-difluorophenyl)-3-methylbutyl]-isothiazolidine 1,1-dioxide (a) (3RS, 4RS)-N-[4-(4-Chlorobenzenesulfonyl-4-(2,5-difluorophenyl)-3-methylbutyl]-3-chloropropane-1-sulfonamide was prepared from (3RS, 4RS)-4-(4-chlorobenzenesulfonyl)-4-(2,5-difluorophenyl)-3-methylbutylamine and 3-chloropropylsulfonyl chloride as in example 1.

m/z (ES$^+$) 514 (MH$^+$).

(b) The aforementioned 3-chloropropanesulfonamide, (0.12 g, 0.24 mmol) in anhydrous toluene (10 ml) was treated with sodium hydride (0.011 g, 0.29 mmol) and the mixture heated at reflux for 96 hours. After cooling, dilution with water (30 ml) and extraction with ethyl acetate (3×30 ml), the combined organic fractions were washed with brine, dried (MgSO$_4$) and evaporated under reduced pressure. The residue was purified by flash chromatography eluting with 10% to 25% ethyl acetate in iso-hexane to give as a mixture of diastereoisomers the title compound as a colourless solid (47 mg, 41%).

$\delta_H$ (400 MHz, CDCl$_3$) 0.85–0.90, 1.32–1.38 (1H, m), 1.05 and 1.26 (total 3H, d, J=7.0 Hz), 1.62–1.69 (1H, m), 2.08–2.23 (1H, m), 2.35–2.39 (2H, m), 2.85–2.98 (1H, m), 3.08–3.24 (4H, m), 3.26–3.46 (1H, m), 4.47–4.54 (1H, m), 6.75–6.78 (1H, m), 6.89–6.92 (1H, m), 7.30–7.34 (2H, m), 7.41–7.52 (3H, m); m/z (ES$^+$) 478 (MH$^+$).

Example 15

(3RS, 4RS)-N-[4-(4-Chloro-benzenesulfonyl)-4-(2,5-difluoro-phenyl)-3-methyl-butyl]-N-methyl-methanesulfonamide a) DIBAL (26.46 ml of a 1M solution in toluene) was added dropwise to a suspension of (3RS, 4RS)-4-(4-chlorobenzenesulfonyl)-4-(2,5-difluorophenyl)-3-methylbutyronitrile (4.67 g, 1.26 mmol) in dichloromethane (10 ml) at −40° C. and under $N_2$. The mixture was stirred for one hour at −40° C. and was then quenched with a saturated aqueous solution of ammonium chloride (20 ml). The phases were separated and the organic phase dried ($Na_2SO_4$) and evaporated under reduced pressure to give as a mixture of diastereoisomers (3RS, 4RS)-4-(4-chlorobenzenesulfonyl)-4-(2,5-difluorophenyl)-3-methylbutyraldehyde as a yellow oil which was used in the next step without further purification (4.6 g, quantitative).

$\delta_H$ (360 MHz, $CDCl_3$) 1.20 and 1.37 (total 3H, d, J=6.6 Hz), 1.60–1.75 (2H, m), 3.09–3.45 (2H, m), 4.82–5.12 (1H, m), 7.10–7.14 (1H, m), 7.26–7.29 (1H, m), 7.49–7.52 (1H, m), 7.65–7.71 (2H, m), 7.77–7.87 (2H, m).

b) To the aldehyde from Step (a) (0.55 g, 1.47 mmol) and methylamine (2M solution in THF, 1.48 ml, 2.95 mmol) in dry dichloromethane (5 ml) was added acetic acid (0.5 ml) followed by sodium triacetoxyborohydride (0.63 g, 2.95 mmol). The mixture was stirred at room temperature for 16 hours before quenching with saturated aqueous sodium bicarbonate solution (10 ml) and separating the phases. The organic phase was dried ($MgSO_4$) and evaporated under reduced pressure to yield as a mixture of diastereoisomers (3RS, 4RS)-N-methyl-[4-(4-chlorobenzenesulfonyl)-4-(2,5-difluorophenyl)-3-methyl-butyl]amine as a gummy yellow solid, which was carried on to the next stage without further purification.

$\delta_H$ (400 MHz, $CDCl_3$) 0.90–0.94, 1.29–1.33 (1H, m; m), 1.07 and 1.35 (total 3H, d, J=6.8 Hz), 1.48–1.57 (1H, m), 2.36 and 2.42 (total 3H, s), 2.58–2.92 (3H, m), 4.46–4.57 (1H, m), 6.72–6.80 (1H, m), 6.90–6.94 (1H, m), 7.26–7.34 (2H, m), 7.40–7.54 (3H, m); m/z ($ES^+$) 388 ($MH^+$).

c) To the amine from Step (b) (0.116 g, 0.3 mmol) in dry dichloromethane (5 ml) was added pyridine (0.060 ml, 0.75 mmol), followed by methanesulfonyl chloride (0.035 ml, 0.45 mmol), and the mixture was stirred at room temperature for 48 hours. After dilution with water (20 ml) and extraction with ethyl acetate (3×20 ml), the combined organic fractions were washed with brine, dried ($MgSO_4$ and evaporated under reduced pressure. The residue was purified by flash chromatography eluting with 10% to 30% ethyl acetate in iso-hexane to give as a mixture of diastereoisomers the title compound as a colourless oil (35 mg, 25%).

$\delta_H$ (360 MHz, $CDCl_3$) 1.45–1.50 (1H, m), 1.65 and 1.85 (total 3H, d, J=6.8 Hz), 1.88–1.96 (1H, m), 2.20–2.31 (2H, m), 3.37 (3H, d, J=5.2 Hz), 3.41 and 3.48 (total 3H, s), 3.87–3.91 (1H, m), 5.08–5.16 (1H, m), 7.32–7.43 (1H, m), 7.48–7.57 (1H, m), 7.89–7.94 (2H, m), 8.01–8.13 (3H, m); m/z ($ES^+$) 466 ($MH^+$).

Example 16

(3RS, 4RS)-N-[4-(4-Chlorobenzenesulfonyl)-4-(2,5-difluorophenyl)-3-methyl-butyl]-N-(2,2,2-trifluoroethyl)-methanesulfonamide prepared by the procedure of Example 15, using 2,2,2-trifluoroethylamine in Step (b).

The product was purified by flash chromatography, eluting with 7% to 20% ethyl acetate in isohexane to give as a mixture of diastereoisomers the title compound as a colourless solid (59% yield).

$\delta_H$ (400 MHz, $CDCl_3$) 1.05 and 1.28 (total 3H, d, J=6.9 Hz), 1.35–1.45 and 1.77–1.86 (total 1H, m), 2.08–2.27 (1H, m), 2.74–2.84 (1H, m), 2.93 and 3.00 (total 3H, s), 3.44–3.57 (2H, m), 3.75–4.02 (2H, m), 4.47–4.51 (1H, m), 6.75–6.82 (1H, m), 6.91–6.98 (1H, m), 7.31–7.34 (2H, m), 7.41–7.52 (3H, m); m/z ($ES^+$) 534 ($MH^+$).

Example 17

(RS)-4-[(4-Chlorobenzenesulfonyl)-(2,5-difluorophenyl)methyl]-1-methanesulfonyl-piperidine a) Triethylamine (1.4 ml, 10 mmol) was added to a stirred solution of tert-butyl 4-hydroxy-1-piperidine-carboxylate (2.0 g, 9.94 mmol) in dichloromethane (40 ml) at −17° C. under nitrogen. Methanesulfonyl chloride (0.85 ml, 11 mmol) was added dropwise and the mixture allowed to warm up to room temperature overnight. The reaction mixture was diluted with dichloromethane (50 ml) and water (100 ml) was added. The organic layer was separated and the aqueous phase was re-extracted with dichloromethane (2×50 ml). The combined organic layers were dried ($MgSO_4$) and evaporated under reduced pressure. The residue was purified by flash chromatography eluting with 50% ethyl acetate in iso hexanes to give tert-butyl 4-methanesulfonyloxy-piperidine-1-carboxylate as a colourless oil (2.47 g, 89%), $\delta_H$ (360 MHz, $CDCl_3$) 1.46 (9H, s), 1.75–1.88 (2H, m), 1.90–2.00 (2H, m), 3.04 (3H, s), 3.25–3.35 (2H, m), 3.65–3.75 (2H, m), 4.88 (1H, m).

b) Sodium hydride (72 mg of a 60% dispersion in mineral oil, 1.8 mmol) was added to a stirred mixture of the mesylate from Step (a) (250 mg, 0.895 mmol) and Intermediate A (542 mg, 1.79 mmol) in THF (8 ml) at 0° C. under nitrogen. The mixture was stirred at 0° C. for 1 hour, at room temperature for 0.75 hour and under reflux for 72 hours. The mixture was partitioned between ethyl acetate (10 ml) and water (10 ml) and the organic layer was separated, washed with brine, dried ($MgSO_4$) and evaporated under reduced pressure. The residue was purified by flash chromatography, eluting with 20% ethyl acetate in iso-hexane to give (RS)-tert-butyl 4-[(4-chlorobenzenesulfonyl)-(2,5-difluorophenyl)methyl]-piperidine-1-carboxylate as a colourless oil (72 mg, 17%).

m/z 386 ($MH^+$-BOC).

c) The product of Step (b) (72 mg, 0.15 mmol) in 96% formic acid (2 ml) was stirred at room temperature under nitrogen for 17 hours. Methanol was added and the mixture was evaporated in vacuo. The residue was dissolved in a small volume of water (10 ml), basified with saturated potassium carbonate solution and extracted with dichloromethane (10 ml). The combined organic extracts were dried ($MgSO_4$) and evaporated in vacuo. This residue was dissolved in dichloromethane (2 ml) under nitrogen and triethylamine (0.029 ml, 0.21 mmol) and methanesulfonyl chloride (0.016 ml, 0.21 mmol) were added sequentially. The resulting mixture was stirred at room temperature for 40 hours and then partitioned between dichloromethane (10 ml) and water (10 ml). The aqueous layer was separated and re-extracted with dichloromethane and the combined organic extracts were dried ($MgSO_4$) and evaporated in vacuo. The residue was purified by flash chromatography, eluting with 40% ethyl acetate in iso hexane to give the title compound as a white solid (37 mg, 58%).

δ$_H$ (360 MHz, CDCl$_3$) 1.39 (1H, m), 1.62–1.76 (2H, m), 2.53–2.83 (7H, m including s at δ 2.78), 3.77 (1H, br d, J=12.1 Hz), 3.88 (1H, br d, J=12.3 Hz), 4.48 (1H, br d, J=8.0 Hz), 6.77 (1H, m), 6.95 (1H, m), 7.31–7.51 (5H, m); m/z 464 (MH$^+$).

Example 18

(RS)-4-[(4-Chlorobenzenesulfonyl)-(2,5-difluorophenyl)-methyl]-1-trifluoromethanesulfonyl-piperidine (a) A solution of ethyl isonipecotate (20.0 g, 127 mmol) and di-tertbutyl dicarbonate (29.1 g, 134 mmol) in dry dichloromethane was stirred at room temperature for 1 hour and the solvent removed under reduced pressure to yield the BOC derivative as a colourless oil (31 g, 91%).

δ$_H$ (360 MHz, CDCl$_3$) 1.26 (3H, t, J=7.1 Hz), 1.46 (9H, s), 1.61–1.66 (2H, m), 1.85 (2H, m), 2.43 (1H, m), 2.83 (2H, m), 3.95–4.05 (2H, m), 4.14 (2H, dd, J=7.1 and 14.2 Hz).

(b) To a solution of the BOC derivative from Step (a) (28 g, 109 mmol) in tetrahydrofuran (100 ml) at −78° C. was added diisobutylaluminium hydride (1M, 222 ml, 222 mmol) slowly and the reaction mixture stirred for 2 hours. The mixture was quenched by the slow addition of methanol (60 ml) and allowed to warm to room temperature, poured into ice-cooled dilute hydrochloric acid (1M, 60 ml), and extracted with ethyl acetate (3×40 ml). The combined organic fractions were washed with brine (50 ml), dried, and concentrated, to yield tert-butyl 4-formyl-piperidine-1-carboxylate (20 g) as a colourless oil which was used without further purification.

c) To a solution of 2,5-difluoro-1-bromobenzene (24.5 g, 127 mmol) in anhydrous tetrahydrofuran (400 ml) at −78° C. was added n-butyllithium (1.6M, 80 ml, 128 mmol). The solution was stirred for 15 minutes tert-butyl-4-formyl-piperidine-1-carboxylate (27.0 g, 127 mmol) added slowly in THF (50 ml). The mixture was allowed to warm to room temperature and stirred for 16 hours, quenched with water (200 ml) and extracted with ethyl acetate (3×150 ml). The combined organics were washed with water (50 ml), dried (MgSO$_4$) and concentrated. The residue was purified by flash chromatography eluting with 3 to 10% ethyl acetate in iso hexanes to yield (RS)-tertbutyl 4-[(2,5-difluorophenyl)-hydroxymethyl]-piperidine-1-carboxylate as a colourless oil (14 g, 34%).

δ$_H$ (360 MHz, CDCl$_3$) 1.12–1.45 (3H, m), 1.44 (9H, s), 1.79–1.90 (2H, m), 2.06 (1H, m), 2.55–2.70 (2H, m), 4.09–4.15 (2H, m), 4.77 (1H, m), 6.95–6.99 (2H, m), 7.15 (1H, m).

d) To a solution of (RS)-tert-butyl-4-[(2,5-difluorophenyl)-hydroxymethyl]-piperidine-1-carboxylate (1.0 g, 3.1 mmol), and bis(4-chlorophenyl)disulfide (1.7 g, 6.1 mmol) in pyridine (10 ml) at room temperature was added tri-n-butylphosphine (1.2 g, 6.1 mmol) and the mixture was stirred at room temperature for 48 hours. The solvent was removed, and the residue taken into ethyl acetate (30 ml) and washed with hydrochloric acid (2N, 10 ml) water (10 ml), dried MgSO$_4$) and evaporated under reduced pressure. The residue purified by flash chromatography eluting with 5 to 20% ethyl acetate in iso hexanes to yield (RS)-tert-butyl 4-[(4-chlorobenzenesulfanyl)-(2,5-difluorophenyl)-methyl]-piperidine-1-carboxylate as an oil (1.1 g, 65%).

δ$_H$ (360 MHz, CDCl 1.15 (1H, m), 1.30–1.40 (1H, m), 1.44 (9H, s), 1.46 (1H, m), 1.85–1.95 (1H, m), 2.15–2.20 (1H, m), 2.55–2.80 (2H, m), 4.00–4.20 (2H, m), 4.31 (1H, d, J=8.8 Hz), 6.86–6.90 (2H, m), 7.05–7.15 (5H, m).

e) To a solution of the sulfide from Step (d) (1.1 g, 2.4 mmol) in dichloromethane (25 ml) was added mCPBA (50%, 2.1 g, 6.1 mmol), and the mixture stirred at room temperature for 16 hours. A saturated aqueous solution of sodium sulfite (20 ml) was added, the organic phases were separated and washed with water (10 ml) dried (MgSO$_4$) and evaporated under reduced pressure. The residue was purified by flash chromatography eluting with 10% ethyl acetate in iso hexanes to give (RS)-tert-butyl 4-[(4-chlorobenzenesulfonyl)-(2,5-difluorophenyl)-methyl]-piperidine-1-carboxylate as a white solid (0.75 g, 65%).

δ$_H$ (360 MHz, CDCl$_3$) 1.15–1.20 (1H, m), 1.44 (9H, s), 1.45–1.56 (2H, m), 2.35–2.45 (1H, m), 2.65–2.90 (3H, m), 4.00–4.20 (2H, m), 4.45 (1H, m), 6.70–6.78 (1H, m), 6.85–6.95 (1H, m), 7.27 (2H, d, J=8.5 Hz), 7.35–7.45 (1H, m), 7.48 (2H, d, J=8.5 Hz).

f) To a solution of (RS)-tert-butyl 4-[(4-chlorobenzenesulfonyl)-(2,5-difluorophenyl)-methyl]-piperidine-1-carboxylate (0.75 g, 1.5 mmol) in dichloromethane (5 ml) was added trifluoroacetic acid (5 ml) and the mixture was stirred at room temperature for 30 minutes. The mixture was washed with sodium hydroxide solution (1N, 5 ml), water (5 ml), dried (MgSO$_4$) and evaporated under reduced pressure to yield (RS)-4-[(4-chlorobenzenesulfonyl)-(2,5-difluorophenyl)methyl]-piperidine as a white solid (0.5 g, 83%).

δ$_H$ (360 MHz, CDCl$_3$) 1.47–1.70 (2H, m), 1.85–1.95 (2H, m), 2.65–2.95 (4H, m), 3.27–3.44 (2H, m), 4.48 (1H, td, J=8.5 Hz), 6.72–6.76 (1H, m), 6.88–6.96 (1H, m), 7.31 (2H, d, J=8.6 Hz), 7.37 (1H, m), 7.48 (2H, d, J=8.6 Hz).

g) To a solution of the piperidine from Step (f) (0.1 g, 0.26 mmol) and triethylamine (0.036 ml, 0.26 mmol) in dichloromethane (3 ml) at −78° C. was added trifluoromethanesulfonic anhydride (0.15 g, 0.32 mmol) and the mixture warmed to −40° C. and stirred at this temperature for 3 hours. The reaction was quenched with aqueous citric acid (10% w/v, 5 ml) diluted with dichloromethane (20 ml) and washed with water (20 ml), dried (MgSO$_4$) and evaporated under reduced pressure. The residue was purified by flash chromatography eluting with 5% ethyl acetate in iso hexanes to yield the title compound as a white solid (0.1 g, 84%).

δ$_H$ (360 MHz, CDCl$_3$) 1.30–1.40 (1H, m), 1.65–1.75 (2H, m), 2.55–2.65 (1H, m), 2.70–2.80 (1H, m), 3.06–3.20 (2H, m), 3.85–4.05 (2H, m), 4.45 (1H, m), 6.70–6.80 (1H, m), 6.90–7.00 (1H, m), 7.31 (2H, d, J=8.6 Hz), 7.40 (1H, m), 7.48 (2H, d, J=8.6 Hz).

The invention claimed is:
1. A compound of formula I:

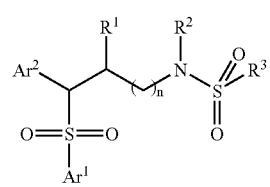

where n is 2, 3 or 4;
Ar$^1$ represents phenyl or heteroaryl, either of which bears 0–3 substituents independently selected from halogen, CN, NO$_2$, CF$_3$, CHF$_2$, OH, OCF$_3$, C$_{1-4}$alkoxy or C$_{1-4}$alkyl which optionally bears a substituent selected from halogen, CN, NO$_2$, CF$_3$, OH and C$_{1-4}$alkoxy;
Ar$^2$ represents phenyl or heteroaryl, either of which bears 0–3 substituents independently selected from halogen, CN, NO$_2$, CF$_3$, CHF$_2$, OH, OCF$_3$, C$_{1-4}$alkoxy or $C_{1-4}$alkyl which optionally bears a substituent selected from halogen, CN, $NO_2$, $CF_3$, OH and $C_{1-4}$alkoxy;

$R^1$ represents $C_{1-4}$alkyl, or together with $R^2$ completes a pyrrolidine, piperidine or homopiperidine ring;

$R^2$ represents H or $C_{1-6}$alkyl which optionally bears a substituent selected from halogen, CN, $NO_2$, $CF_3$, OH and $C_{1-4}$alkoxy; or together with $R^1$ completes a pyrrolidine, piperidine or homopiperidine ring; or together with $R^3$ completes a tetrahydroisothiazole-1,1-dioxide ring; and $R^3$ represents phenyl, naphthyl or heteroaryl, any of which may bear up to 3 substituents selected from halogen, CN, $NO_2$, $CF_3$, $CHF_2$, OH, $OCF_3$, $C_{1-4}$alkoxy, $C_{1-4}$alkoxycarbonyl, $C_{2-6}$acyl, $C_{2-6}$acyloxy, $C_{2-6}$acylamino, amino, $C_{1-4}$alkylamino, di($C_{1-4}$alkyl)amino or $C_{1-4}$alkyl which optionally bears a substituent selected from halogen, CN, $NO_2$, $CF_3$, OH and $C_{1-4}$alkoxy; or $R^3$ represents $CF_3$ or a non-aromatic hydrocarbon group of up to 6 carbon atoms optionally bearing one substituent selected from halogen, CN, $CF_3$, OH, $OCF_3$, $C_{1-4}$alkoxy, $C_{1-4}$alkoxycarbonyl, $C_{2-6}$acyl, $C_{2-6}$acyloxy, $C_{2-6}$acylamino, amino, $C_{1-6}$alkylamino, di($C_{1-4}$alkyl)amino or phenyl, naphthyl or heteroaryl, any of which may bear up to 3 substituents selected from halogen, CN, $NO_2$, $CF_3$, $CHF_2$, OH, $OCF_3$, $C_{1-4}$alkoxy, $C_{1-4}$alkoxycarbonyl, $C_{2-6}$acyl, $C_{2-6}$acyloxy, $C_{2-6}$acylamino, amino, $C_{1-4}$alkylamino, di($C_{1-4}$alkyl)amino or $C_{1-4}$alkyl which op bears a substituent selected from halogen, CN, $NO_2$, $CF_3$, OH and $C_{1-4}$alkoxy; or $R^3$ together with $R^2$ completes a tetrahydroisothiazole-1,1-dioxide ring;

or a pharmaceutically acceptable salt thereof.

2. A compound according to claim 1 of formula II:

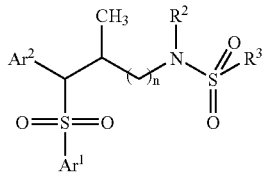

II where n, $Ar^1$, $Ar^2$, $R^2$ and $R^3$ are as defined in claim 1; or a pharmaceutically acceptable salt thereof.

3. A compound according to claim 1 of formula III:

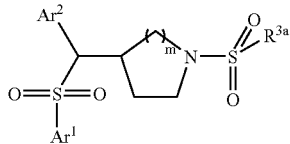

III wherein m is 1, 2 or 3;

$R^{3a}$ represents $R^3$ which does not form a ring with $R^2$;

and $Ar^1$, $Ar^2$ and $R^3$ are as defined in claim 1;

or a pharmaceutically acceptable salt thereof.

4. A compound according to claim 1 wherein $Ar^1$ is 4-chlorophenyl or 4-trifluoromethylphenyl and $Ar^2$ is 2,5-difluorophenyl.

5. A pharmaceutical composition comprising a compound according to claim 1, or a pharmaceutically acceptable salt thereof, and a pharmaceutically acceptable carrier.

6. A method of treatment of a subject suffering from Alzheimer's Disease which comprises administering to that subject an effective amount of a compound according to claim 1 or a pharmaceutically acceptable salt thereof.

7. A method of preparing a compound according to claim 1 in which $R^2$ does not form a ring with $R^3$ comprising reaction of an amine (IV) with $R^{3a}$—$SO_2Cl$:

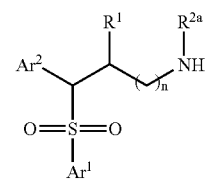

IV where $R^{2a}$ represents $R^2$ which does not complete a ring with $R^3$, $R^{3a}$ represents $R^3$ which does not complete a ring with $R^2$, and n, $Ar^1$, $Ar^2$, $R^1$, $R^2$ and $R^3$ are as defined in claim 1.

8. A method of preparing a compound according to claim 1 in which $R^2$ and $R^3$ together complete a tetrahydroisothiazole-1,1-dioxide comprising reaction of an amine:

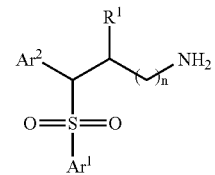

where n, $Ar^1$, $Ar^2$ and $R^1$ are as defined in claim 1, with L—$(CH_2)_3$—$SO_2Cl$ where L represents a leaving group, followed by intramolecular alkylation of the resulting sulphonamide nitrogen.

* * * * *